United States Patent [19]
Sutherland et al.

[11] Patent Number: 4,780,557
[45] Date of Patent: Oct. 25, 1988

[54] METHOD OF PREPARATION OF (SUBSTITUTED-THIO)ALKYL ISOTHIOCYANATES

[75] Inventors: George W. Sutherland; Stephen J. Kuhn, both of Sarnia, Canada

[73] Assignee: The Dow Chemical Company, Midland, Mich.

[21] Appl. No.: 89,468

[22] Filed: Aug. 26, 1987

[51] Int. Cl.$^4$ .......................................... C07C 119/042
[52] U.S. Cl. ........................................................ 558/19
[58] Field of Search ........................................... 558/19

[56] References Cited
U.S. PATENT DOCUMENTS 3,160,649 12/1964 Hasselstrom et al. ................. 558/19
3,584,028  6/1971 Argabright et al. ................... 558/19
4,479,903 10/1984 Dauplaise ............................. 558/19

FOREIGN PATENT DOCUMENTS 2550263  5/1977 Fed. Rep. of Germany ........ 558/19
7009109 12/1970 Netherlands ........................... 558/19
1324635  7/1973 United Kingdom ................... 558/19
2062645 12/1979 United Kingdom ................... 558/19

OTHER PUBLICATIONS

*Acta Chemica Scandinavica II*, Anders Kjaer, Bo Christensen, 1298-1307.
*Organic Chemistry of Bivalent Sulfur*, VI, 64, E. E. Reid (ed, Chemical Publishing Co., Inc. (1965)).
Uch. Zap. Azerb. Bos. Univ., Ser. Khim. Nauk. (#1), 50-51 (1972).
J5 8090-546-A, Kinjirushi Wasabik.
J5 7134-461, Nihon Noyaku KK.

*Primary Examiner*—Alan L. Rotman
*Assistant Examiner*—Robert C. Whittenbaugh
*Attorney, Agent, or Firm*—Paula Sanders Ruhr

[57] ABSTRACT

A one-step process for the preparation of (substituted-thio)alkyl isothiocyanates in high yield comprising contacting a haloalkyl sulfide with a thiocyanate salt in the absence of a catalyst under reaction conditions sufficient to produce the desired (substituted-thio)alkyl isothiocyanate is disclosed. Examples of compounds produced by this process include $CH_3SCH_2CH_2NCS$ and $n\text{-}C_6H_{13}SCH_2CH_2NCS$.

The compounds produced by this process are useful as intermediates in the synthesis or ore flotation chemicals such as substituted thiocarbamates or thioureas.

15 Claims, No Drawings

METHOD OF PREPARATION OF (SUBSTITUTED-THIO)ALKYL ISOTHIOCYANATES

BACKGROUND OF THE INVENTION

This invention relates to processes for the preparation of (substituted-thio)alkyl isothiocyanates.

Isothiocyanates are known to have various utilities depending on what substituents are present. Allyl isothiocyanates are taught to be useful as intermediates in the preparation of thionocarbamates useful in sulfide ore flotation in U.S. Pat. No. 4,479,903 to Dauplaise. Alkyl-thioalkyl isothiocyanates are taught to be useful as spices in U.S. Pat. No. 3,160,649 to Hasselstrom et al.

One of the problems associated with the preparation of these compounds is the difficulty of obtaining exclusively the isothiocyanate isomer rather than the thiocyanate isomer or a mixture of both isomers. Some R-SCN compounds are readily isomerized to R-NCS by the simple addition of heat. This is particularly true when R represents —$CH_3$ or —$CH_2CH=CH_2$. However, it has been recognized that, when R represents a saturated alkyl radical other than the methyl radical, isomerization does not occur in a practical way merely with the addition of heat. See, e.g., Organic Chemistry of Bivalent Sulfur, Vol. VI, Ch. 1, p. 64, ed. E. E. Reid, Chemical Publishing Co., Inc. (1965).

A study of the synthesis of alkyl-2-thiocyanatoethyl-sulfides in Uch. Zap. Azerb. Gos. Univ., Ser. Khim. Nauk, No. 1, 50–51 (1972) determined that these thiocyanates are very stable and do not isomerize to the isothiocyanates after heating up to 200° C. for five hours.

It is generally recognized that isomerization to the isocyanate isomer may be obtained in some cases by the use of a catalyst. In U.S. Pat. No. 3,584,028, a method of preparation of organic isocyanates requiring the use of certain halide catalysts, such as alkali metal bromides, alkali metal iodides, and alkaline earth metal bromides, is disclosed. In Organic Chemistry of Bivalent Sulruf, supra, it is taught that certain salts, for example cadmium iodide, will facilitate isomerization of thiocyanates.

Due to the difficulty of isomerizing thiocyanates to isothiocyanates, typical methods of preparing isothiocyanates involve preparing the isothiocyanate directly.

Kjaer and Christensen in Acta. Chem. Scand., 11, 1298–1307 (1957) teach that isothiocyanates corresponding to the formula $CH_3S(CH_2)_nNCS$ (n=2–9) can be prepared from the corresponding chloride in a three-step procedure resulting in a yield of less than 50 percent. Their process involves reaction of the chloride with potassium phthalimide: reduction of this product to the corresponding amine via hydrazine hydrate: and, finally, reaction of the amine with thiocarbonyl chloride to obtain the isothiocyanate.

It is also known that isothiocyanates may be produced from the reaction of acid chlorides and potassium or ammonium thiocyanates.

What is needed is a process for synthesizing isothiocyanates that is simple, uses readily available reactants and gives high yields.

SUMMARY OF THE INVENTION

The present invention is a process for the preparation of (substituted-thio)alkyl isothiocyanates wherein a haloalkyl sulfide is contacted with a thiocyanate salt in the absence of a catalyst under reaction conditions such that the corresponding (substituted-thio)alkyl isothiocyanate is produced in good yield. It is surprising that the isothiocyanate rather than the thiocyanate is obtained without the addition of a catalyst.

The (substituted-thio)alkyl isothiocyanates produced by the process of this invention are useful as intermediates in the synthesis of ore flotation chemicals, such as substituted thiocarbamates or thioureas.

DETAILED DESCRIPTION OF ILLUSTRATIVE EMBODIMENTS

Reactants useful in the process of the present invention are haloalkyl sulfides and thiocyanate salts.

The haloalkyl sulfides useful in the process of the present invention comprise a divalent sulfur atom to which are bonded (1) an alkyl halide substituent such that the halide and sulfur atoms are separated by at least two and not more than three carbon atoms and (2) a hydrocarbyl substituent.

The preferred haloalkyl sulfides correspond to the general formula:

$$R^1S(CR^2R^3)_nX$$

wherein $R^1$ is $C_{1-20}$ hydrocarbyl: each $R^2$ and each $R^3$ are independently H or $C_{1-20}$ hydrocarbyl: X is chlorine, bromine or iodine: and n is 2 or 3. Examples of suitable hydrocarbyl substituents include straight or branched chain alkyl, aryl, or aralkyl such as methyl, butyl, hexyl, and phenyl. It is preferred that n equals 2 and that X is chlorine. It is also preferred the $R^1$ is $CH_3$ or $n$-$C_6H_{13}$ and that each $R^2$ and each $R^3$ are independently hydrogen or $CH_3$. It is most preferred that $R^2$ and $R^3$ are each hydrogen.

Many of the haloalkyl sulfides, such as $CH_3SCH_2CH_2Cl$, useful in the practice of this invention are readily available on an industrial scale. The haloalkyl sulfides may also be prepared by methods known in the art such as the radically initiated reaction of RSH plus olefin or by reaction of RSH with an olefin oxide followed by reaction with anhydrous or concentrated HCl. For a discussion of methods of preparation, see, e.g., Reid, Organic Chemistry of Bivalent Sulphur Vol. II, Chapter 4, Chemical Publishing Co., N.Y. (1960) and references included therein.

The thiocyanate salts useful in the practice of this invention correspond to the general formula, $M(SCN)_m$, wherein M is a Group IA or Group IIA metal ion or an ammonium ion and m is 1 or 2 depending on whether M is a Group IA or IIA metal ion. It is preferred that M is sodium, potassium or ammonium and that m is 1. It is more preferred than M is potassium or sodium and it is most preferred that M is potassium. The thiocyanate salts described herein are readily available on an industrial scale. The thiocyanate may also be generated in situ, if desired, by the reaction of MCN with sulfur.

Any temperature and pressure at which the reaction will proceed is useful in the practice of this invention. It is preferred that temperatures of at least about 50° C. are used and that temperatures no greater than about 200° C. are used. Preferred temperatures are at least about 75° C. and no greater than about 175° C. It is most preferred that the reaction take place at a temperature of at least 130° C. and no greater than about 170° C. Atmospheric pressure is used for the sake of convenience. Also for convenience, the reaction is conducted in the presence of air.

The reagents may be added in any order and amount. Any molar ratio of haloalkyl sulfide to thiocyanate at which the reaction will proceed is useful in the process of this invention. It is preferred that the molar ratio of haloalkyl sulfide to thiocyanate be at least about 1:1 and no greater than about 1:20. It is more preferred that this ratio be no greater than about 1:10 and it is most preferred that it be about 1:1.

A solvent is advantageously used in the process of this invention. It is preferred to use an inert polar solvent. In this context, inert means that the solvent will not react with either the starting materials or the products. Alcohols are not preferred due to their reactivity with the isothiocyanates produced by the process of this invention. Examples of suitable inert polar solvents include acetonitrile, nitrobenzene, N,N-dimethylaniline, N,N-dimethylformamide and dimethylsulfoxide. It is preferred to use N,N-dimethylformamide as a solvent.

The reaction is allowed to proceed until virtually all of the reactant is converted. Reaction times may range from about five minutes to about twenty-four hours. Preferred reaction times range from about 0.25 hour to about 5 hours. It is more preferred that the reaction proceed for approximately 0.5 to 3 hours.

Conversion of reactant in the practice of this invention is near quantitative and it is preferred that conversion be at least about 99 percent. Selectivity to the isothiocyanate isomer is, at least in part, a function of the length of time the reaction is allowed to proceed. When the reaction is allowed to proceed for from one to two hours or more, selectivity to the isothiocyanate isomer is at least about 35 percent and preferably at least about 75 percent. It is more preferred that selectivity to the isothiocyanate isomer is at least about 95 percent and most preferred that it be at least about 98 percent.

Yield of product obtained in the practice of this invention is at least about 35 percent and is preferred to be at least about 50 percent. It is more preferred that the yield be at least about 75 percent and most preferred that it be at least about 80 percent The reduction of yield from the at least about 97 percent indicated by the conversion and selectivity information is due to the formation of non-volatile tars during the isomerization period.

The process of this invention may be operated as a batch or continuous operation. In using a continuous operation, it is necessary to adjust reactor design to accommodate the residence time required for the isomerization process which may take from five minutes up to about five hours. This may be accomplished by adjusting reactor size, rate of flow of reactants, and/or reaction temperature to control both residence time and time needed for reaction.

The following examples are provided for illustrative purposes only and do not limit the invention in any way. Unless stated otherwise, all parts and percentages are given by weight.

EXAMPLE 1

Preparation of (Methylthio) Ethyl Isothiocyanate $CH_3SCH_2CH_2Cl$ is added to a solution of KSCN in refluxing N,N-dimethylformamide in a three-necked round-bottomed flask equipped with a thermometer, a condenser and a dropping funnel in proportions such that the $CH_3SCH_2CH_2Cl$:KSCN molar ratio is 1:1. The reaction mixture is heated in a heating bath and the temperature is maintained at about 155° C. Upon the completion of the addition of $CH_3SCH_2CH_2Cl$, the solution is refluxed an additional five minutes. The KCl formed in the reaction is removed by filtration and $CH_3SCH_2CH_2NCS$ is isolated by distillation at reduced pressure. The amount of $CH_3SCH_2CH_2NCS$ isolated is measured by gas chromatography/mass spectrometry.

This procedure is repeated twice with the only difference being that refluxing is allowed to continue twenty-five minutes and seventy-five minutes respectively. The results of these experiments are shown in Table I below.

TABLE I

|  | Reaction Time (min) | | |
|---|---|---|---|
|  | 5 | 25 | 75 |
| % $CH_3SCH_2CH_2SCN$ | 67.5 | 11.8 | 0.5 |
| % $CH_3SCH_2CH_2NCS$ | 32.5 | 88.2 | 99.5 |

EXAMPLE 2

Preparation of (n-Hexylthio) Ethyl Isothiocyanate

Example 1 is repeated with the exception that n-$C_6H_{13}SCH_2CH_2Cl$ is used as a reagent instead of $CH_3SCH_2CH_2Cl$ and the reaction is allowed to proceed for seventy-five minutes. The product is isolated by distillation at reduced pressure and analyzed by gas chromatography/mass spectrometry which shows that the product is 0.7 percent n-$C_6H_{13}SCH_2CH_2SCN$ and 97.0 percent n-$C_6H_{13}SCH_2CH_2NCS$.

EXAMPLE 3

Preparation of (n-Hexylthio) Propyl Isothiocyanate n-$C_6H_{13}SCH_2CH_2CH_2Cl$ is added to a solution of KSCN in refluxing N,N-dimethylformamide at about 155° C. in an amount sufficient to provide a n-$C_6H_{13}SCH_2CH_2Cl$:KSCN molar ratio of about 1:1. Upon completion of the addition of n-$C_6H_{13}SCH_2CH_2CH_2Cl$, the reaction mixture is refluxed an additional 0.5 hours. The amount of n-$C_6H_{13}SCH_2CH_2CH_2NCS$ formed was measured by gas chromatography/mass spectrometry.

This procedure is repeated twice with the only difference being that refluxing is allowed to continue 4.5 hours and 20.5 hours respectively. The results of these experiments are shown in Table II below.

TABLE II

|  | Reaction Time (hr.) | | |
|---|---|---|---|
|  | 0.5 | 4.5 | 20.5 |
| % $C_6H_{13}SCH_2CH_2CH_2SCN$ | 77.5 | 32.0 | 2.3 |
| % $C_6H_{13}SCH_2CH_2CH_2NCS$* | 2.5 | 32.0 | 39.0 |

*Additional products are observed, e.g., $C_6H_3SCN$, $C_6H_{13}NCS$, $C_6H_{13}S(CH_2)_3SC_6H_{13}$ and others, which are not reported here.

EXAMPLE 4

Preparation of n-$C_6H_{13}SCH_2CH(CH_3)NCS$ and n-$C_6H_{13}SCH(CH_3)_2CH_2NCS$ To a solution of KSCN in refluxing N,N-dimethylformamide at about 155° C. is added n-$C_6H_{13}SCH_2CH(CH_3)Cl$ containing about 3 weight percent of n-$C_6H_{13}SCH(CH_3)_2CH_2Cl$ such that the Cl:SCN molar ratio is about 1:1. The reaction mixture is allowed to continue refluxing an additional 0.05 hour after the addition of n-$C_6H_{13}SCH_2CH(CH_3)Cl$ and n-$C_6H_{13}SCH(CH_3)_2CH_2Cl$ is completed. The product is isolated by distillation at reduced pressure and analyzed by gas chromatography/mass spectrometry. This process is repeated three times with the only difference being that the reaction is allowed to continue 0.25, 1.0 and 2.0 hours respectively. These results are shown in Table III below.

TABLE III

|  | Reaction Time (hr) | | | |
| --- | --- | --- | --- | --- |
|  | 0.05 | 0.25 | 1.0 | 2.0 |
| % $C_6H_{13}SCH_2CH(CH_3)SCN$ | 59.7 | 0.68 | 0.54 | 0.31 |
| % $C_6H_{13}SCH_2CH(CH_3)NCS$ | 11.2 | 54.0 | 71.9 | 77.6 |
| % $C_6H_{13}SCH(CH_3)CH_2SCN$ | ND | ND | ND | ND |
| % $C_6H_{13}SCH(CH_3)CH_2NCS$ | 18.4 | 42.0 | 24.3 | 19.3 |

ND = Not detected

The above results clearly show that the process of the present invention is a versatile and effective method for the production of (substituted-thio)alkyl isothiocyanates.

What is claimed is:

1. A process for the preparation of (substituted-thio)alkyl isothiocyanates comprising contacting a haloalkyl sulfide with a thiocyanate salt in the absence of a catalyst under reaction conditions such that the corresponding (substituted-thio)alkyl isothiocyanate is produced.

2. The process of claim 1 wherein the haloalkyl sulfide corresponds to the formula:

$$R^1S(CR^2R^3)_nX$$

wherein $R^1$ is $C_{1-20}$ hydrocarbyl; each $R^2$ and each $R^3$ are independently H or $C_{1-20}$ hydrocarbyl; X is chlorine, bromine or iodine; and n is 2 or 3.

3. The process of claim 2 wherein n is 2.

4. The process of claim 2 wherein the thiocyanate salt corresponds to the general formula, $M(SCN)_m$, wherein M is a Group IA or Group IIA metal ion or an ammonium ion and m is 1 or 2.

5. The process of claim 4 wherein M is potassium and m is 1.

6. The process of claim 1 wherein the temperature is at least about 75° C. and no greater than about 175° C.

7. The process of claim 6 wherein the temperature is at least about 130° C. and no greater than about 170° C.

8. The process of claim 1 wherein the pressure is maintained at about atmospheric.

9. The process of claim 1 wherein a solvent is employed.

10. The process of claim 9 wherein the solvent is N,N-dimethylformamide.

11. The process of claim 1 wherein the conversion of haloalkyl sulfide is about 99 percent.

12. The process of claim 11 wherein the selectivity to (substituted-thio)alkyl isothiocyanate is at least about 75 percent.

13. The process of claim 12 wherein the selectivity to (substituted-thio)alkyl isothiocyanate is at least about 98 percent.

14. The process of claim 11 wherein the overall yield is at least about 80 percent based on the haloalkyl sulfide starting material.

15. The process of claim 1 wherein the process takes place in one step.

* * * * *

UNITED STATES PATENT AND TRADEMARK OFFICE
CERTIFICATE OF CORRECTION

PATENT NO. : 4,780,557
DATED : October 25, 1988
INVENTOR(S) : George W. Sutherland and Stephen J. Kuhn It is certified that error appears in the above-identified patent and that said Letters Patent is hereby corrected as shown below:

Col. 1, line 40, "Sulruf" should correctly appear as --Sulfur--.

Col. 2, line 17, insert -- aprotic -- between "polar" and "solvents";
line 42, insert a period after "percent".

Col. 4, lines 37-38, "n-$C_6H_{13}SCH_2CH_2Cl$:KSCN" should correctly appear as -- n-$C_6H_{13}SCH_2CH_2CH_2Cl$:KSCN --.

Col. 5, lines 26-27, delete "under reaction conditions such that the corresponding" and insert -- in the presence of a polar aprotic solvent at a temperature from at least about 50°C to no greater than about 200°C and recovering the desired --;
lines 27-28, delete "is produced".

Signed and Sealed this

First Day of August, 1989

Attest:

DONALD J. QUIGG

Attesting Officer

Commissioner of Patents and Trademarks